(12) United States Patent
Mizuno et al.

(10) Patent No.: US 6,930,227 B1
(45) Date of Patent: Aug. 16, 2005

(54) CAMELLIA SINENSIS GENE ENCODING A CAFFEINE SYNTHESIS ASSOCIATED N-METHYL TRANSFERASE WITH 7-METHYLXANTHINE N3 METHYL TRANSFERASE, THEOBROMINE N1 METHYL TRANSFERASE, AND PARAXANTHINE N3 METHYL TRANSFERASE ACTIVITIES AND USE THEREOF

(75) Inventors: Misako Mizuno, Ibaraki (JP); Hiroshi Ashihara, Tokyo (JP); Kouichi Mizuno, Ibaraki (JP); Tatsuhito Fujimura, Ibaraki (JP)

(73) Assignee: Mitsui Chemicals, Inc., Tokyo (JP)

(*) Notice: Subject to any disclaimer, the term of this patent is extended or adjusted under 35 U.S.C. 154(b) by 0 days.

(21) Appl. No.: 09/577,657

(22) Filed: May 25, 2000

(30) Foreign Application Priority Data

May 26, 1999 (JP) .......................................... 11/146358

(51) Int. Cl.[7] .......................... A10H 5/00; C12N 15/82; C12N 5/10; C12N 15/54
(52) U.S. Cl. ...................... 800/298; 800/278; 435/419; 435/320.1; 536/23.2
(58) Field of Search .............................. 435/320.1, 419, 435/468; 800/298, 278, 286; 536/23.2, 23.6

(56) References Cited

U.S. PATENT DOCUMENTS 6,075,184 A * 6/2000 Stiles et al. .................. 800/298

OTHER PUBLICATIONS

Kato, M. et al. Accession No. AB031280, Aug. 31, 2000.*

Flavell, R. B. et al., "Instability of Transgenes in Plants and its Implications for Plant Breeding." 1995, In: Induced Mutations and Molecular Techniques for Crop Improvement, International Atomic energy Agency, Vienna, pp. 13–22.*

Sweetlove, L. J. et al., "Starch metabolism in tubers of transgenic potato (*Solanum tuberosum*) with increased ADP-glucose pyrophosphorylase." 1996, Biochem. J., vol. 320, pp. 493–498.*

Thiele, A. et al., "Heterologous Expression of Arabidopsis Phytochrome B in Transgenic Potato Influences Photosythetic Performance and Tuber Development." 1999, Plant Physiology, vol. 120, pp. 73–81.*

Klann, E. M. et al., "Antisense Acid Invertase (TIV1) Gene Alters Soluble Sugar Composition and Size in Transgenic Tomato Fruit," 1996, Plant Physiol., vol. 112, pp. 1321–1330.*

Tang, G. et al., "Antisense Repression of Vacuolar and Cell Wall Invertase in Transgenic Carrot Alters Early Plant Development and Sucrose Partitioning." The Plant Cell, vol. 11, pp. 177–189.*

Colliver, S. P. et al., "Differential modification of flavonoid and isoflavonoid biosynthesis with an antisense chalcone sythase construct in transgenic Lotus corniculatus." 1997, Plant Molecular Biology, vol. 35, pp. 509–522.*

Hill, M. A. and Preiss, J. "Functional Analysis of Conserved Histidines in ADP–Glucose Pyrophosphorylase from *Escherichia coli*." 1998, Biochemical and Biophysical Res. Comm., vol. 244, pp. 573–577.*

Lazar, E. et al., "Transforming Growth Factor a: Mutation of Aspartic Acid 47 and Leucine 48 Results in Different Biological Activities." 1988, Molecular and Cellular Biology, vol. 8, pp. 1247–1252.*

Broun, P. et al., "Catalytic Plasticity of Fatty Acid Modification Enzymes Underlying Chemical Diversity of Plant Lipids." 1998, Science, Viol. 282, pp. 1315–1317.*

Bowie, J. U. et al., "Deciphering the Message in Protein Sequences: Tolerance to Amino Acid Substitutions." 1990, Science, vol. 247, pp. 1306–1310.*

Kato, M. et al., "Caffeine synthase gene from tea leaves." 2000, Nature, vol. 406, pp. 956–957.*

Kato, Misako, et al. "*Purification and Characterization of Caffeine Synthase from Tea Leaves*" 120 Plant Physiology pp 579–586 (1999).

* cited by examiner

Primary Examiner—Anne Kubelik
(74) Attorney, Agent, or Firm—Burns, Doane, Swecker & Mathis, LLP (57) ABSTRACT

The present invention makes it possible to efficiently produce an N-methyl transferase with 7-methylxanthine N3 methyl transferase, theobromine N1 methyl transferase, and paraxanthine N3 methyl transferase activities that can be utilized as an industrial, food, or medical enzyme. In addition, the present invention makes it possible to modify the caffeine biosynthesis metabolism of caffeine producing plants, plant tissues, or plant cells, thereby efficiently producing caffeine metabolism based compounds or modifying the production of caffeine in the plants.

11 Claims, 1 Drawing Sheet

FIGURE 1

CAMELLIA SINENSIS GENE ENCODING A CAFFEINE SYNTHESIS ASSOCIATED N-METHYL TRANSFERASE WITH 7-METHYLXANTHINE N3 METHYL TRANSFERASE, THEOBROMINE N1 METHYL TRANSFERASE, AND PARAXANTHINE N3 METHYL TRANSFERASE ACTIVITIES AND USE THEREOF

FIELD OF THE INVENTION

The present invention relates to an N-methyl transferase, one of the enzymes constituting a caffeine metabolic system, which is a polypeptide simultaneously having activities of three methyl transferases: 7-methyl xanthine N3 methyl transferase, theobromine N1 methyl transferase, and paraxanthine N3 methyl transferase; variants of the N-methyl transferase; DNA molecules or RNA molecules having nucleotide sequences encoding any one of the N-methyl transferase and the variants thereof; vectors using these molecules; cells transformed with the vectors; and uses thereof.

DESCRIPTION OF THE RELATED ART

Caffeine is a purine alkaloid contained in Theaceae *Camellia* plants such as *Camellia sinensis* or Rubiaceae *Coffea* plants such as *Coffea arabica* or the like, and is used as a raw material for medicines and/or food additives. At present, caffeine is produced by extraction from caffeine producing plants including the foregoing plant species or by organic synthesis. In addition, in items such as tea or coffee, in order to alleviate or enhance their stimulus, a reduction or increase in the content of caffeine and its intermediates is attempted using classical bleeding techniques or the like.

Figure 1:
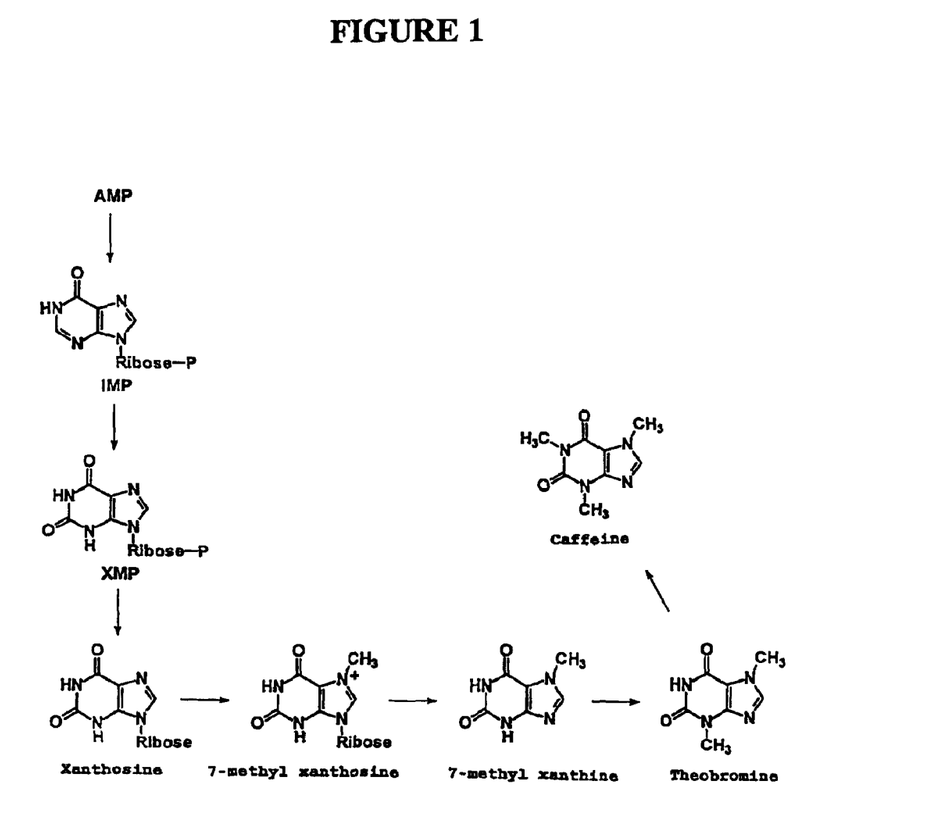
FIG. 1 is the reaction pathway indicating that caffeine is biosynthesized from xanthosine through three stages of N-methylation.

In Phytochemistry, 31, 2575-(1992), there is disclosed a reaction pathway indicating that caffeine is biosynthesized from xanthosine through three stages of N-methylation. This was determined by conducting experiments using a $^{14}$C-tracer. This reaction path is shown in FIG. 1.

Enzyme activities for catalyzing this methylation, that is, methyl transferase activities, were first reported by a study using coarse extraction of tea leaves in 1975 (Biochem. J. 146, 87-(1975)). Although attempts have been made to purify methyl transferase from coffee (Phytochemistry, 37, 1577-(1994)), the purification magnification is very low. For tea, partial purification of methyl transferase was reported (Physiol. Plant., 98, 629-(1996)), but no enzyme protein was isolated.

As described above, concerning the amino acid sequence of the enzyme in a caffeine metabolic system, that is, an N-methyl transferase that catalyzes a two-stage methylation reaction from 7-methyl xanthine through theobromine to caffeine that is a final reaction of caffeine biosynthesis, neither the amino acid sequence nor the DNA encoding the amino acid sequence is known in the prior art.

SUMMARY OF THE INVENTION

It is an object of the present invention to provide N-methyl transferase, one of the enzymes that constitute a caffeine metabolic system useful for caffeine synthesis, simultaneously having enzyme activities of 7-methyl xanthine N3 methyl transferase, theobromine N1 methyl transferase, and paraxanthine N3 methyl transferase; a DNA or RNA molecule encoding the N-methyl transferase useful for enhancement or suppression of caffeine production in microorganisms or plants, and vectors or the like using the same.

For example, all or part of the DNA molecule according to the present invention is incorporated in microorganisms or plant cells in a form of sense or antisense, thereby making it possible to achieve the following objects:

(1) Efficiently producing N-methyl transferase that can be utilized as an enzyme for industrial, food, or medical use;

(2) Efficiently producing compounds related to caffeine metabolism by modifying caffeine biosynthesis and metabolism of caffeine-producing plants, plant tissues or plant cells; and (3) Modifying caffeine biosynthesis and metabolism of caffeine-producing plants, plant tissues, or plant cells, thereby modifying the production rate of the caffeine metabolism related compounds.

The present inventors conducted N-terminal amino acid sequence analysis of an N-methyl transferase, as a polypeptide simultaneously having activities of three enzymes, 7-methyl xanthine N3 methyl transferase, theobromine N1 methyl transferase and paraxanthine N3 methyl transferase, from cotyledons of tea. Based on the result, a DNA probe was prepared and a target DNA molecule was successfully isolated by RT-PCR techniques and 5' RACE techniques using this probe.

Next, the DNA molecule was integrated into a vector and inserted into *Escherichia coli* to express a large amount of a polypeptide derived from the DNA molecule. When the expressed polypeptide was recovered and its enzymological properties were investigated, the same reaction as that of the polypeptide having activities of the above described three N-methyl transferases isolated from cotyledons of tea, that is, caffeine production from paraxanthine was observed. It was thus verified that the DNA molecule has a gene that encodes an N-methyl transferase, one of the enzymes of the caffeine synthesis system, simultaneously having activities of the above-described three N-methyl transferase.

In plants in which N-methylation is carried out for a xanthosine or analogous compound, or a xanthine or analogous compound, using S-adenosyl methionine (SAM) as a methyl-group donor, polypeptides having the activity of the N-methyl transferase according to the present invention or the same enzyme activity as the transferase and DNAs that encode these peptides are estimated to be contained. Using the method according to the present invention, the N-methyl transferase or the substantially same enzyme as the transferase and DNA or RNA molecules that encode these transferases can be obtained from these plants.

The present inventors achieved the present invention based on the above findings. That is, the present invention includes the following aspects.

The first DNA molecule according to the present invention is characterized by comprising any one of the following nucleotide sequences:

(a) a nucleotide sequence that encodes an N-methyl transferase, as a polypeptide having an amino acid sequence of SEQ ID NO: 1 of the sequence listing and having enzyme activities of 7 methyl xanthine N3 methyl transferase, theobromine N1 methyl transferase, and paraxanthine N3 methyl transferase; and (b) a modified nucleotide sequence obtained by nucleotide replacement, deletion, or insertion in the above-described nucleotide sequence (a) within a range where a polypeptide encoded by the nucleotide sequence (a) can maintain the enzyme activity.

It is preferable that the modified nucleotide sequence (b) can be hybridized with the complementary sequence of the nucleotide sequence (a) under stringent conditions.

The first RNA molecule according to the present invention is characterized by comprising any one of the following nucleotide sequences:

(a) a nucleotide sequence that encodes an N-methyl transferase, as a polypeptide having an amino acid sequence of SEQ ID NO: 1 of the sequence listing and having enzyme activities of 7 methyl xanthine N3 methyl transferase, theobromine N1 methyl transferase, and paraxanthine N3 methyl transferase; and (b) a modified nucleotide sequence obtained by nucleotide replacement, deletion, or insertion in the above-described nucleotide sequence (a) within a range where a polypeptide encoded by the nucleotide sequence (a) can maintain the enzyme activity.

It is preferable that the modified nucleotide sequence (b) can be hybridized with the complementary sequence of the nucleotide sequence (a) under stringent conditions.

A vector for expression of the N-methyl transferase according to the present invention is characterized by comprising the above-described first DNA or RNA molecule and a constitution to express the N-methyl transferase encoded by the DNA or RNA molecule, in plant cells. Host cells can be transformed using the expression vector to obtain transformed cells. Further, the transformed cells are cultured, thereby making it possible to produce N-methyl transferase having the above enzyme activities.

Another aspect of a DNA molecule according to the present invention is the second DNA molecule having a sequence complementary to all or a part of the nucleotide sequence of the above first DNA molecule, characterized by that the second DNA molecule is capable of inhibiting the enzyme activities of the plant cells when it is introduced into plant cells having the enzyme activities and expressed in the plant cells.

Another aspect of a RNA molecule according to the present invention is the second RNA molecule having a sequence complementary to all or a part of the nucleotide sequence of the above first RNA molecule, characterized by that the second RNA molecule is capable of inhibiting expression of the N-methyl transferase activities of the plant cells when it is introduced into plant cells having the N-methyl transferase activities and its expression is conducted.

An aspect of a vector according to the present invention is characterized by comprising one of the above DNA molecules and RNA molecules. This vector can be provided so as to have a function either to make expression of the N-methyl transferase possible or to inhibit expression of the N-methyl transferase in a microorganism or a plant, which transferase has the three activities of 7-methyl xanthine N3 methyl transferase, theobromine N1 methyl transferase, and paraxanthine N3 methyl transferase, as described above.

Using the vector, microorganisms, plant cells, plant tissues, or plant bodies can be transformed, and the obtained transformants are included in the present invention. A secondary metabolite in plants can be produced using the transformed plant cells, plant tissues, or plant bodies. In addition, the composition of the secondary metabolite in the transformed plants can be modified using the plant cells, plant tissues, or plant bodies.

The N-methyl transferase according to the present invention is a polypeptide having enzyme activities of 7-methyl xanthine N3 methyl transferase, theobromine N1 methyl transferase, and paraxanthine N3 methyl transferase, characterized by having:

(a) an amino sequence of SEQ ID NO: 1 of the sequence listing; or (b) a modified amino acid sequence obtained by replacement, insertion, or deletion of amino acids for the amino acid sequence of SEQ ID NO: 1 of the sequence listing within a range where the above-described enzyme activities are not lost, but maintained.

As to this modified amino acid sequence (b), it is preferable that the DNA encoding the amino acid sequence (a) and the DNA encoding this modified amino acid sequence (b) can be hybridized under stringent conditions.

According to the present invention, there is provided a DNA molecule and an RNA molecule encoding the N-methyl transferase, which is:

i) one of the enzymes constituting a caffeine synthesis system, ii) useful for caffeine synthesis and modification of the composition of caffeine produced in microorganisms or plants, and iii) a polypeptide simultaneously having the three enzyme activities of 7-methyl xanthine N3 methyl transferase, theobromine N1 methyl transferase, and paraxanthine N3 methyl transferase.

DETAILED DESCRIPTION OF THE INVENTION AND PREFERRED EMBODIMENTS

The N-methyl transferase according to the present invention is a polypeptide simultaneously having enzyme activities of 7-methyl xanthine N3 methyl transferase, theobromine N1 methyl transferase, and paraxanthine N3 methyl transferase.

As for the N-methyl transferase, that having an amino acid sequence indicated by SEQ ID NO: 1 and that having a modified amino acid sequence obtained by carrying out amino acid replacement, insertion, or deletion within a range where desired N-methyl transferase activity is not damaged in the amino acid sequence of SEQ ID NO: 1 can be mentioned. That is, polypeptides having an amino acid sequence of SEQ ID NO: 1 having the desired N-methyl transferase activity as described above and those having a modified sequence are referred to as N-methyl transferase.

The above polypeptide having the modified amino acid sequence itself has functions substantially identical to N-methyl transferase of cotyledons of tea, and has high homology with an amino acid sequence of SEQ ID NO: 1 at a site associated with enzyme activities.

In general, between a plurality of enzymes having the identical functions, it is well-known that homology of the amino acid sequence other than a site indispensable for enzyme activities is very low (Kawagoe et al., Proc. Natl. Acad. Sci. USA, 93, 12082-(1996)). Therefore, even in the case where the entire homology is low, transferase having high homology at a site associated with activities can be classified as N-methyl transferase.

In comparing the entire amino acid sequence, there can be exemplified a modified amino acid sequence which can provide a polypeptide having the desired N-methyl transferase and homology of 15% or more, preferably homology of 30% or more, more preferably homology of 45% or more, and further preferably homology of 60% or more, and still further preferably homology of 75% or more, the most preferably homology of 95% or more against the amino acid sequence of SEQ ID NO: 1.

In the case where modification against the amino acid sequence of SEQ ID NO: 1 as the basis are defined at a level of nucleotide sequence encoding the modified amino acid sequence, there can be provided a modified nucleotide sequence having homology of 40% or more, preferably homology of 60% or more, more preferably homology of 75% or more, further preferably homology of 90% or more, still further preferably homology of 95% or more against the nucleotide sequence encoding the amino acid sequence of SEQ ID NO: 1.

A nucleotide sequence encoding the N-methyl transferase according to the present invention, that is, an N-methyl transferase gene can contain a nucleotide sequence encoding one of the an amino acid sequences of SEQ ID NO: 1. A specific example thereof can include the DNA sequence of SEQ ID NO: 2 and the RNA sequence of SEQ ID NO: 3. A nucleotide sequence having homology as described above with the N-methyl transferase genes as the basis is also included with the gene encoding the N-methyl transferase according to the present invention.

As a modified amino acid sequence maintaining the desired N-methyl transferase activities, its preferable examples include that encoded by a modified nucleotide sequence, which can hybridize under stringent conditions with the nucleotide sequence encoding the amino acid sequence of SEQ ID NO: 1 as the basis.

In addition, as the modified N-methyl transferase gene, that capable of hybridizing with the nucleotide sequence encoding the amino acid sequence of SEQ ID NO: 1 under stringent conditions can be preferably utilized in practice. A specific example thereof can include DNA molecules capable of being hybridized under stringent conditions to a nucleotide sequence of SEQ ID NO: 2; and RNA molecules capable of being hybridized under stringent conditions to a nucleotide sequence of SEQ ID NO: 3.

Hybridization under these stringent conditions can be carried out, for example, by the method described in Molecular Cloning: Cold Spring Harbor Laboratory Press, Current Protocols in Molecular Biology; Wiley Interscience. As a commercially available system, a GeneImage system (Amersham) can be exemplified. Specifically, hybridization can be carried out by the following operation.

A membrane to which DNA or RNA molecules to be tested has been transferred is treated for hybridization using a labeled probe in a hybridization buffer specified by the protocol in accordance with product protocols. The composition of hybridization buffer consists of 0.1 wt. % SDS; 5 wt. % Dextran sulfate; 1/20 volume of a blocking reagent included in the kit, and 2 to 7×SSC. A blocking reagent is used by preparing 100×Denhardt's solution, 2% (weight/volume) Bovine serum albumin, 2% (weight/volume) FicII™ 400, 2% (weight/volume) polyvinyl pyrrolidone at a 5-fold concentration, and diluting them to 1/20. 20×SSC is a 3M sodium chloride and 0.3M citric acid solution. SSC is preferably used at a concentration of 3 to 6×SSC, and further preferably used at a concentration of 4 to 5×SSC.

The hybridization temperature ranges from 40 to 80° C., more preferably 50 to 70° C., and further preferably 55 to 65° C. Incubation for several hours or one night is carried out, followed by washing using a washing buffer. The washing temperature is preferably equal to room temperature, and more preferably is a temperature during hybridization. The composition of the washing buffer is a 6×SSC+0.1 wt. % SDS solution, more preferably 4×SSC+ 0.1 wt. % SDS solution, further preferably 2×SSC+0.1 wt. % SDS solution, still further preferably 1×SSC+0.1 wt. % SDS solution, and the most preferably 0.1×SSC+0.1 wt. % SDS solution. A membrane is washed by such washing buffer, whereby the DNA molecules or RNA molecules in which the probe is hybridized can be identified by utilizing a label employed for the probe.

Modification may occur in nature or may be artificially-generated by site mutation in the nucleotide sequence.

DNA molecules having N-methyl transferase genes according to the present invention can be separated from cells producing N-methyl transferase according to the present invention by utilizing PCR technique as described in "Plant PCR test protocols" (another volume of cell engineering, plant cell engineering series 2) Shujynsha (1995), in which an oligonucleotide specifically hybridized for DNA molecules for encoding N-methyl transferase, for example, is employed as a primer.

Specifically, a linker is bonded with cDNA synthesized from mRNA, and PCR is carried out between the linker and the DNA encoding an amino acid sequence constituting the N-methyl transferase, whereby the full-length sequence of the target cDNA can be isolated.

DNA molecules encoding the N-methyl transferase obtained by such hybridization technique or PCR technique have homology with the N-methyl transferase gene of SEQ ID NO: 2 at least at a site used for isolation. The homology used herein denotes homology of 15% or more, preferably homology of 30% or more, more preferably homology of 45% or more, further preferably homology of 60% or more, still further preferably homology of 75% or more, still furthermore homology of 90% or more, and the most preferably homology of 95% or more in comparing the amino acid sequence encoded by the respective N-methyl transferase genes. However, even if homology with N-methyl transferase becomes 15% or less as a result of deletion, addition, and replacement of a plurality of residues of amino acid to be encoded, it is estimated that some of the obtained N-methyl transferase genes maintain a region indispensable to the functions of N-methyl transferase, and substantially encode proteins having their functions similar to N-methyl transferase.

All of the organisms employed for isolating DNA molecules or RNA molecules having nucleotide sequences (genes) encoding N-methyl transferase according to the present invention can be used, as long as they produce caffeine or its precursor. They can include Theaceae *Camellia* plant such as tea, Rubiaceae *Coffea* plant such as coffee, Sterculiaceae *Cola* plant such as *Cola* or the like.

An RNA molecule including an N-methyl transferase gene according to the present invention can be obtained by connecting a DNA encoding the N-methyl transferase, which can be prepared by the above described method, in the desired direction at the operable location on the downstream side of a promoter such as Sp6 promoter or T7 promoter, which is recognized by RNA polymerase, to prepare a recombinant molecule and translating the recombinant molecule by Sp6 RNA polymerase or T7 polymerase to obtain the desired RNA molecule. The RNA molecule can be also obtained by introducing a DNA or RNA encoding the N-methyl transferase into a plant virus or inserting a DNA or RNA encoding the N-methyl transferase into a vector carrying an appropriate expression cassette, as described below, so that the DNA or RNA is connected to the expression cassette in the desired direction at the operable location to prepare a recombinant molecule and introducing the recombinant molecule into a host microorganism or plant so that the RNA encoding the N-methyl transferase can be formed in the host using the transcription activity of the host.

DNA molecules complementary with all or a part of the DNA molecules having the N-methyl transferase genes or RNA molecules complementary with all or a part of the RNA molecules having N-methyl transferase genes can be used as DNA or RNA molecules for inhibition or suppression of N-methyl transferase expression in plant cells, as long as these molecules have a function to inhibit expression of the N-methyl transferase peculiar to the host plant cells when these molecules are expressed in the host plant cells.

According to the present invention, the part of the N-methyl transferase gene as the basis for complementation to the DNA or RNA molecule denotes a site which can be used to provide a complementary sequence as a basis to form mRNA for inhibition (i.e., antisense RNA) in the host cells. This mRNA for inhibition is formed in host cells, the RNA is bonded with mRNA for expressing N-methyl transferase in host cells, and the expression of N-methyl transferase in the host cells is inhibited. This site is necessary for forming such antisense mRNA, which is, for example, at least 14 bases in length.

DNA molecules for forming the antisense mRNA can include, for example, DNA molecules complementary to all or a part of the nucleotide sequence of SEQ ID NO: 2, and antisense RNA molecules include RNA molecules complementary to all or a part of the nucleotide sequences of SEQ ID NO: 3. DNA molecules or RNA molecules complementary with all or a part of the modified sequence capable of being hybridized with these nucleotide sequences of SEQ ID NOs: 2 and 3 under stringent conditions can also be used for such a purpose.

The DNA molecules having high homology with these inhibiting DNA molecules or RNA molecules and having desired inhibiting or restricting functions can also be utilized. Here, high homology denotes homology of 60% or more, preferably homology of 75% or more, further preferably homology of 90% or more, and the most preferably homology of 95% or more in comparing the respective nucleotide sequences.

These inhibiting DNA molecules or RNA molecules themselves may not always encode N-methyl transferase according to the present invention.

Another aspect of the nucleotide sequence for inhibiting N-methyl transferase according to the present invention is directed to a nucleotide sequence having one or more sites with homology to the N-methyl transferase gene, but do not encode N-methyl transferase. The N-methyl transferase peculiar to the host cells can be inhibited by replacing this nucleotide sequence with the N-methyl transferase gene of the host cells to be deleted.

With respect to expression of the N-methyl transferase gene or expression of the DNA molecules having functions for inhibiting or restricting expression of the N-methyl transferase gene or N-methyl transferase in the host cells, an example utilizing plant cells as host cells will be described hereinafter.

For expression in plant cells, there can be utilized a method for introducing into host plant cells an expression cassette and transforming the host cells, which expression cassette includes: (i) a promoter enabling transcription from DNA to mRNA in the host cell; (ii) a DNA fragment containing an N-methyl transferase gene bonded with the downstream side of the promoter in the sense or antisense direction or a DNA fragment having functions for inhibiting the expression of N-methyl transferase; and (iii) a terminator sequence containing a polyadenylation site required for stabilization of transcribed products bonded with the downstream side of these DNA fragments as required.

Such expression cassette and a vector containing this cassette are the subject of the present invention.

The expression cassette can contain a promoter for constitutively or inductively expressing the inserted DNA. In addition, this expression cassette can have a replication origin for its replication in the plant cells as required.

Promoters for constitutive expression include, for example, a 35S promoter for cauliflower mosaic virus, rice actin promoter, and the like. In addition, promoters for inductive expression include, for example, promoters known to be expressed by external factors such as infection or invasion of mold, bacteria or virus, low temperature, high temperature, dry, anaerobic conditions, specific compound spraying, or the like. Such promoters include a promoter of chitinase genes of rice expressed, for example, by infection or invasion of mold, bacteria or virus; a promoter of PR protein genes; a promoter of "lip19" genes of rice induced by low temperature; a promoter of "HSP182" genes of *Capsella bursa-pastoris* induced by high temperature; a promoter of "rab" genes of rice induced by dry; a promoter of alcohol dehydrogenase gene of corn induced by anaerobic conditions or the like. In addition, the promoter for the chitinase genes of rice and the promoter for PR protein genes of tobacco are induced by specific compounds such as salicylic acid or the like, and the rice "rab" gene promoter is induced by spraying abscisic acid of plant hormone.

Alternatively, as a promoter for expressing DNA inserted into the expression cassette, a promoter derived from any of the N-methyl transferase genes per se can be used.

A specific example of promoter isolation can include a method for selecting genome DNA fragments and specifying the DNA at the upward section of the gene by utilizing the hybridization technique in which all or a part of N-methyl transferase genes is employed as a probe.

In order to prepare for introduction of recombinant DNA molecules in the expression cassette into plants, there can be utilized a number of cloning vectors containing a replication signal in *E. coli* and a marker gene(s) for selection of the transformed *E. coli* cells. Examples of such vectors include pBR322, pUC system, Mi3mp system, or the like. A target sequence can be introduced at a proper restriction enzyme cutting site. In order to clarify characteristics of the obtained plasmid DNA, analysis of the restriction enzyme cutting site, gel electrophoresis, and other biochemical, molecule-biological methods are generally used. After each operation has been completed, the plasmid DNA is cut and can be bonded with another DNA. The sequence of each plasmid DNA can be cloned in the same plasmid or another plasmid.

In order to introduce the expression cassette into plant cells, a variety of techniques can be used. These techniques include transformation of plant cells with T-DNA using *Agrobacterium tumefaciens* or *Agrobacterium rhizogenes* as transformation factors; direct induction into protoplast (injection method, electroporation method, or the like), Particle gun method, or the like and any other possibility.

In direct introduction into protoplast, no vector is particularly required. For example, a simple plasmid such as a pUC derivative can be employed. Some methods for introducing target genes into plant cells may require another DNA sequence. For example, when a Ti or Ri plasmid is employed for transformation of plant cells, it is preferable to connect at least the right-end sequence of the T-DNA region for the Ti and Ri plasmids, mostly the sequences on both ends, so as to be adjacent regions of genes to be introduced.

When *Agrobacterium* is employed for transformation, an expression cassette to be introduced is required to be cloned in a specific plasmid, that is, in an intermediate vector or a binary vector. The intermediate vector is not replicated in the *Agrobacterium*. The intermediate vector is moved into the *Agrobacterium* by a helper plasmid or by electroporation. The intermediate vector has a region homologous with the sequence of T-DNA, and thus, is incorporated into the Ti or Ri plasmid of *Agrobacterium* by homologous recombination. *Agrobacterium* used as a host is required to include a vir region. In general, the Ti or Ri plasmid includes the vir region, and T-DNA can be moved to plant cells by way of the functions of the region.

On the other hand, the binary vector can be replicated and maintained in *Agrobactrilium*. Thus, when the binary vector is incorporated into *Agrobacterium* by the helper plasmid or electroporation technique, T-DNA on the binary vector can be moved to plant cells by the functions of the vir region of the host.

The intermediate vector or binary vector including the thus-obtained expression cassette and microorganisms such as *Escherichia coli* or *Agrobacterium* including these vectors are the subject of the present invention.

The transformed plant cells can be converted into a plant tissue or a plant body by experiencing a reproduction process. The reproduction methods depend on the kinds of plant cells, and include the Fujimura et al. method for rice (Plant Tissue Culture Lett., 2. 74-(1995)); the Shillito et al. method for corn (Bio/Technology, 7, 581-(1989)); and the Akama et al. method for *Capsella bursa-pastoris* (Plant Cell Rep., 12, 7-(1992)), or the like.

According to the present invention, the term "plant body" means the whole individual organism classified into plant or organ parts thereof, such as leaves, stems, roots, flowers, fruits, seeds, and the like.

For the plant body produced by these methods or the plant body obtained from its breeding catalyst (for example, seeds, stems, cuttings, or the like), an expression quantity of N-methyl transferase according to the present invention changes in comparison with a wild-type plant body producing caffeine or its precursor; a change in generation quantity of caffeine metabolism system compounds due to modification of metabolism of the host plant or a change in production rate of the caffeine metabolism system compound group due to modification of metabolism of the host plant takes place. The thus-obtained transgenic plant is the subject of the present invention. The plants according to the present invention includes specific tissues or cells of plants such as leaves, flowers, fruits, seeds, or the like.

In addition, in recent years, from the study of post-translation gene silencing of plants, it has been found that the expression of target genes can be restricted by utilizing the intrinsic protection mechanisms of the plant for exotic nucleic acids such as virus (Cell, 95, 177–187 (1998), Chemistry and Biology, 37, 532-(1999) and protein nucleic acid enzyme, 44, 1396-(1999)). According to this study, in the case where DNA virus or RNA virus or the like invades plants, the plants transcribe aberrant RNA from these molds, and double-stranded RNA is formed sequentially specifically with the transcribed product of the intrinsic sequence that plants possess. This double-stranded RNA is decomposed by RNase, thereby making it possible to restrict the expression of target genes (Cell, 96, 303-(1999)). One of the essential characteristics of this method is that a sequence whose expression is to be restricted does not always need to be transformed to the target plant. In addition, further characteristics of this method is that, if a target nucleic acid is introduced into part of the plant (low-order leaf or the like) by infection or the like, its effect widens the entire plant body. A specific expression-restricting method is to cause double-stranded RNA including all or part of the sequence of the target gene or the sequence having high homology or *Agrobacterium* having the double-stranded DNA to be infected with the low-order leaf of the plant. Here, high homology denotes homology of 60% or more, preferably homology of 75% or more, further preferably homology of 90% or more, and the most preferably homology of 95% or more in comparing the respective base sequences.

In the plant body subjected to this method, an expression quantity of the N-methyl transferase protein according to the present invention changes in comparison with a wild-type plant body producing caffeine or its precursor. In addition, change in expression quantity of the caffeine metabolism compounds due to modification of metabolism of the host plant or change in production rate of caffeine metabolism system compound group due to modification of metabolism of the host plant takes place. The thus-obtained plant is the subject of the present invention. The plants used in this invention include specific tissues or cells of plants such as leaves, flowers, fruits, seeds, or the like.

Plants producing caffeine with the SAM being a methyl group donor can include caffeine-producing plants, including Theacea *Camellia* plants such as tea; Rubiaceae *coffea* plants such as coffee; Sterculiaceae *Cola* plants such as *Cola*.

Microorganisms for introducing DNA that encodes the N-methyl transferase, thereby expressing a large amount of the N-methyl transferase proteins according to the present invention, can include bacteria such as *E. coli, Bacillus subtilis*, or the like; and virus, such as Baculoviridae.

In addition, any plants producing caffeine or its precursor can be used as plants into which a DNA that encodes the N-methyl transferase according to the present invention in the sense or antisense form to obtain transformed plants for the purposes of improving productivity for a specific compound and changing a production ratio of a specific compound group by modifying the metabolism in host cells.

The production of secondary metabolites relating to the caffeine synthesis system and the composition of the secondary metabolites produced by these transformants can be modified by culturing plant cells or plant tissues transformed with the vector of the above-described constitution or cultivating plants transformed in the same manner. As the secondary metabolites, for example, at least one compound selected from the group consisting of 7-methyl xanthine, paraxanthine, theobromine, and caffeine can be mentioned.

As supply sources of plant cells, plant tissues, or plant bodies used for transformation, for example, a *Camellia* plant, a *Coffea* plant, *Cola* plant, *Ilex* plant, *Neea* plant, *Firmiana* plant, *Paulinia* plant, or *Therbroma* plant body can be mentioned as plant bodies for transformation.

These plants can include Theaceae *Camellia* plants such as tea; Rubiaceae *coffea* plants such as coffee; Sterculiaceae *Cola* plants, such as *Cola* or the like.

Further, in the N-methyl transferase according to the present invention, structurally analogous compounds such as 7-methyl xanthine as well as theobromine can be methylated. Thus, even if they are not the above kinds of plants, the method according to the present invention is applicable to plants containing structurally-analogous compounds of xanthine thereof.

As a result of enzymological study, it is clear that the N-methyl transferase according to the present invention has the following basic properties.

Molecular weight: 41,000 (SDS-PAGE), 61,000 (gel filtration)

Isoelectric point: 4.5 to 5.0 (Chromatofocusing)

Optimum pH: 8.5

Km value: 21 μM (SAM) or 24 μM (paraxanthine)

Inhibitor: SAH (S-adenosyl homocysteine)

Reaction mechanism: SAM+Paraxanthine–SAH caffeine

EXAMPLES

Hereinafter, the present invention will be described in more detail by way of Examples. The scope of the present invention is not limited to these Examples.

mM KCl; 20% (v/v) glycerin. After deionization was carried out the fraction was adsorbed to a cathode ion exchange column Shodex IEC QA-824 (8×25 mm) for the exclusive use for high performance liquid chromatography balanced by the same buffer solution. After the column was washed by the same buffer solution, the adsorbed protein was eluted by a linear concentration gradient 30 ml of 20–750 mM KCl (dissolved in the 50 mM Tris-hydrochloric acid buffer solution (pH 8.5) containing 2 mM EDTA-$Na_2$; 2 mM 2-mercapto-ethanol; and 20% (v/v) glycerin). The active fraction was collected, deionized, and adsorbed by adenosine-agarose (1 ml) that is an affinity column balanced by the same buffer solution after being dissolved in 50 mM Tris-hydrochloric acid buffer solution (pH 8.5) containing 2 mM EDTA-$Na_2$; 2 mM 2-mercapto-ethanol; and 20% (v/v) glycerin. The active fraction was eluted by the 50 mM Tris-hydrochloric acid buffer solution (pH 8.5) containing 0.2 M NaCl; 2 mM EDTA-$Na_2$; 2 mM 2-mercapto-ethanol; and 20% (v/v) glycerin. The obtained fraction was subjected to gel filtration using HiLoad Superdex 200 (16×600 mm) balanced by the 50 mM Tris-hydrochloric acid buffer solution (pH 8.5) containing 2 mM 2-mercapto-ethanol; 150 mM KCl; 20% (v/v) glycerin, and a finally refined sample was obtained. Table 1 summarizes a change in rate activity in the refining process of N-methyl transferase.

TABLE 1

| Steps | Fraction | Liquid quantity (ml) | Total activity (pkat) | Total protein mass (mg) | Specific activity (pKat/mg) | Degree of Purification | Production rate (%) |
|---|---|---|---|---|---|---|---|
| 1 | Crude Extract | 930 | 6330 | 581 | 10.9 | 1.0 | 100 |
| 2 | Ammonium sulfate | 33.8 | 3410 | 155 | 22.0 | 2.0 | 53.9 |
| 3 | Hydroxy apatite | 23.0 | 2630 | 28.9 | 91.0 | 8.0 | 41.5 |
| 4 | Shodex IEC QA-824 | 7.5 | 1070 | 4.82 | 221 | 20.3 | 16.9 |
| 5 | Adenosine - agarose | 2.0 | 202 | 0.08 | 2530 | 232 | 3.2 |
| 6 | Superdex 200 | 5.8 | 228 | 0.04 | 5700 | 523 | 3.6 |

Example 1

Preparation of Purified Fraction of N-Methyl Transferase

First, second, and third leaves of tea leaves (*Camellia sinensis* var. Yabukita) collected in Makurazaki City, Kagoshima Prefecture, Japan, in May, 1997 were frozen using liquid nitrogen, and preserved at −80° C. This material of 100 g was milled by adding 5 mM EDTA-$Na_2$ of 1,000 ml; 2.5 mM 2-mercapto-ethanol; 5% (v/v) glycerin; 1 mg aprotinin; 0.5% (w/v) sodium ascorbate; and 50 mM sodium phosphate buffer solution (pH 7.3) containing 2.5% (w/v) insoluble polyvinyl polypyrrolidone, and was filtrated through three-layer gaze. Then, the filtered liquid was centrifuged (10,000 g, 15 minutes), and a supernatant was obtained. Then, a 50–80% saturated ammonium sulfate fraction was prepared from the supernatant. This fraction was deionized using Sephadex G-25; was dissolved in 10 mM sodium phosphate buffer solution (pH 7.2) containing 2 mM EDTA-$Na_2$; 2 mM 2-mercapto-ethanol; 20% (v/v) glycerin; and then, was adsorbed to hydroxy apatite column (15×160 mm) equilibrated with the same buffer solution; and an active fraction was eluted using a 10–200 mM linear concentration gradient of 200 ml of the sodium phosphate buffer solution containing 2 mM EDTA-$Na_2$; 2 mM 2-mercaptoethanol; 20% (v/v) glycerin. The active fraction was collected, the precipitate was recollected by 80% unsaturated ammonium sulfate, and the fraction was dissolved in 50 mM Tris-hydrochloric acid buffer solution (pH 8.4) containing 2 mM EDTA-$Na_2$; 2 mM 2-mercapto-ethanol; 20

Example 2

Analysis of the Amino Acid Sequence of N-Methyl Transferase Refined Fraction

The finally-purified sample was transferred to a PVDF membrane using a Semidry Blotting apparatus after SDS-polyacrylamide gel electrophoresis. A site at which N-methyl transferase was transferred was cut away and an amino acid sequence of an N-terminus was analyzed using an ABI protein sequencer. The result is shown in SEQ ID NO:4 (Phe Met Asn Arg Gly Glu Xaa Glu Ser Ser Tyr Ala Gln Asn Ser Gln Phe Thr Gln Val).

Example 3

A 19 residue oligonucleotide NMT-1 and Not I-(dT) 18 primer (Pharmacia Biotech) based on a 7-amino acid residue of the N-terminus of the oligonulceotide for cDNA cloning of N-methyl transferase was employed as a probe. The sequence of NMT-1 is shown in SEQ ID NO:5.

Example 4

Synthesis of Single Strand cDNA for Cloning of N-methyl Transferase (I) Isolation of Total RNA Young tea leaves of 5 g were milled under the existence of liquid nitrogen using rod or mortar. After sublimation of the liquid nitrogen, 3M LiCl of 50 ml and 8 M urea were added, and was further milled by polytron. After the milled leaves were statically placed one night at 4° C. and were centrifuged at 12,000 rpm for 15 minutes. The precipitate was suspended in a 0.5% SDS, 10 mM Tris-hydrochloric buffer solution (pH 7.6) to be about 10 ml in total amount. The suspended precipitate was mixed by adding 10 ml phenol/chloroform solution, and was centrifuged at 12,000 rpm for 10 minutes. A 1/10 volume of 3M sodium acetate solution (pH 4.8) and then 2 volumes of ethanol were added to the supernatant, the mixture was statically placed at −80° C. for one hour. Centrifugation was carried out at 4° C. and 12,000 rpm for 10 minutes, 70% ethanol was added to the precipitate separated from the supernatant to form suspension, and centrifugation was carried out again. The supernatant was removed, and the residue was dried up by a vacuum pump. The precipitate thus obtained was dissolved in 1.5 ml water, 150 $\mu$l of 3M sodium acetate solution (pH 4.8) was added thereto, and further, 1.5 ml of phenol/chloroform solution was added thereto to be fallen and mixed. Then, centrifugation was carried out at 12,000 rpm for 10 minutes. Ethanol of x2 volume was added to the supernatant, and was statically placed at −80° C. for 20 minutes. Then, centrifugation was carried out at 40° C. and 12,000 rpm for 10 minutes. To the thus obtained precipitate, 70% ethanol was added, and centrifugation was carried out again. The precipitate was dried up by te vacuum pump, was dissolved in 200 $\mu$l water, and thus, a fraction of total RNA was obtained.

(2) Isolation of MRNA

The total RNA (2 mg) obtained by the above-described method was subjected to heat treatment at 65° C. for 5 minutes, and then was mixed with solution A of the same volume of 2-fold concentration (10 mM Tris-hydrochloric acid buffer solution (pH 7.5); 1 mM $Na_2$-EDTA; 0.1% SDS; 0.5 M NaCl). 0.1 g of oligo (dT)-Cellulose Type 7 (Pharmacia) was immersed in 2 ml of solution B (10 mM Tris-hydrochloric acid buffer solution (pH 7.5); 1 mM-EDTA-$Na_2$; 0.1% SDS; 0.1 M NaCl), and the suspension was poured into a blue chip filled with glass wool at its tip end, and was washed by 2.5 ml of 0.1N NaOH. Then, 5 ml of solution A was poured and balanced. Total RNA was applied to this column, and 3 ml of solution A and 4 ml of solution B were poured. Then, mRNA was eluted by 3 ml of solution C (10 mM Tris-hydrochloric buffer solution (pH 7.5), 1 mM-EDTA-$Na_2$, and 0.05% SDS). The eluted solution was condensed by ethanol precipitation and was dried up. Then, the solution was dissolved in water and was preserved at −80° C.

(3) Synthesis of Single-Stranded cDNA 190 ng of MRNA was acutely cooled for 3 minutes immediately after heat treatment at 65° C. for 10 minutes. This sample was employed as a template, and a single-stranded cDNA was synthesized using First-Strand cDNA Synthesis Kit (Pharmacia). The synthesized cDNA was preserved at −20° C.

Example 5

Cloning of N-Methyl Transferase Genes Using the RT-PCR Technique

The following reaction solution containing the single-stranded cDNA prepared by the above described method as a template was prepared. Oligonucleotide NMT-1 having 19 residues (5'-ttYatgaaYMgIggIgIgaRg-3') based on the N-terminus 7 amino acid residues of the purified N-methyl transferase in Example 2 and NotI-(dt)18 primer (Pharmacia Biotech) were used as the primers. This reaction solution was reacted at 95° C. for 1 minute using Peltier Thermal cycler PTC-200 (Funakoshi) and then PCR was carried out under conditions in which one cycle included the steps of 95° C./1 minute, 45° C./1 minute, and 72° C./2 minutes, respectively and reacted by 30 cycles, and the reacted product was obtained.

Template cDNA: 3 $\mu$l
10×buffer: 5 $\mu$l
2.5 mM NTP: 8 $\mu$l
NMT-1: 1 $\mu$l (50 pmol)
NotI-(dT) 18: 1 $\mu$l (50 pmol)
$H_2O$: 31 $\mu$l
ExTaq (TAKARA): 1 $\mu$l Example 6

Sub-cloning to Plasmid Vector

Electrophoresis of the reaction product obtained in Example 5 was carried out in TAE using 0.8% agarose gel, a band of the obtained target product was cut away, and DNA was recollected from a gel using GENE CLEAN (Funakoshi). The recollected DNA was transformed to *Escherichia coli* DH5a after ligation with pT7blue vector (Novagen). After color selection was carried out using X-gal, liquid culture was carried out in the LB culture medium containing Ampicillin, and plasmid was extracted using the alkali-SDS technique. The presence or absence of the insert was verified by agarose electrophoresis.

Example 7

Nucleotide Sequence Determination

Primer extension was carried out in the following reaction solution using the isolated plasmid. The reaction conditions are as follows. After reaction at 96° C./1 minute, PCR in which one cycle included the steps of 96° C./0.2 minute, 50° C./0.1 minute, and 60° C./4 minutes, respectively, and repeated by 25 cycles was carried out. Ethanol precipitation was carried out for the reaction solution, the obtained DNA was dissolved in Template suppression reagent, and was analyzed using ABI-310 genetic analyzer. In order to determine a sequence at the center of the target DNA, there was used a plasmid in which the DNA fragment obtained by treating DNA with StyI was sub-cloned in pUC19. These primer sequences are shown in SEQ ID Nos: 6 and 7.

Composition of the Primer Extension Reaction Solution
Plasmid DNA (20 ng): 2 $\mu$l
Premix: 4 $\mu$l
Primer: 1 $\mu$l
$H_2O$: 3 $\mu$l Example 8

Isolation of 5' Upstream Area of N-Methyl Transferase mRNA Using 5' the RACE Technique 5'-Full RACE Core Set (TAKARA) was employed for isolation of the 5' upstream area. The sequences of the primers used for SEQ ID NOs: 8 to 17 are shown below.

With the 1st strand of cDNA synthesized by the method described in Example 4, after decomposition of hybrid RNA and cycling of the single-stranded cDNA with ligation reaction, PCR reaction was carried out based on normal technique using the primers of SEQ ID NOs: 8 to 12 or SEQ ID NOs: 13–17, and the reacted product was obtained. A band of the reacted product was separated by acrylamide electrophoresis, DNA was recollected from a gel, and was sub-cloned to the pT7blue vector. Then, the nucleotide sequence of the DNA inserted by the technique similar to those in Examples 6 and 7 was determined.

The DNA sequence of the N-methyl transferase gene thus obtained from tea and the amino acid sequence encoded by the gene are shown as SEQ ID NO: 18.

Example 9

Expression of N-Methyl Transferase in *Escherichia coli*

The following operation was carried out in order to re-incorporate the isolated N-methyl transferase gene into the expression vector pET23d (Novagen).

PCR was carried out under the following conditions using the pT7blue vector into which the isolated N-methyl transferase gene DNA obtained in Example 6 as a template and the primers of SEQ ID NOs: 18 and 19, respectively, and the reaction product was obtained.
Reaction Conditions:

After reaction at 95° C./1.5 minutes, PCR in which one cycle included the steps of 95° C./1 minute, 52° C./1 minute, and 72° C./1 minutes, respectively, and repeated by 30 cycles were carried out.

Separately, a fragment obtained by treating the isolated N-methyl transferase gene DNA fragment with NcoI and EcoRI was inserted into a pET23d vector. Then, the above PCR product was inserted into the NcoI site of this pET23d vector to construct an N-methyl transferase expression plasmid. This plasmid was transformed to *Escherichia coli* BL21 (DE3). After the obtained *Escherichia coli* was cultured at 37° C. for 2 hours, IPTG was added thereto so as to be 0.3 mM in final concentration, and 3-hour culture was further carried out at 30° C. After culturing had been completed, cells were collected and the cells from 3 ml culture solution were subjected to supersonic treatment for 1 minute with interval in 0.2 ml 10 mM Tris-hydrochloric acid buffer solution (pH 7.5), 0.1 M NaCl, 1 mM EDTA-$Na_2$. Then, centrifugation was carried out at 14,000 rpm for 10 minutes, and the obtained supernatant was employed as an enzyme solution.

Regarding the sequencing in Examples 7 and 8, the nucleotide sequence of the DNA fragment including the N-methyl transferase gene obtained in this example has the sequence of SEQ ID NO:2 and the corresponding RNA nucleotide sequence has the sequence of SEQ ID NO:3. The corresponding amino acid sequence of the N-methyl transferase is shown as SEQ ID NO:1.

The reaction solution for N-methyl transferase measurement was prepared as follows. 10 μl of enzyme solution was added to 100 mM Tris-hydrochloric acid buffer solution (pH 8.5), 0.2 mM $MgCl_2$, 0.2 mM paraxanthine, 4 μM S-adenosyl methionine (0.9 kBq), and the volume of the reaction solution was 100 μl. Reaction was carried out at 27° C. for 10 minutes, the obtained $^{14}$C-caffeine was extracted by adding 1 ml chloroform thereto and the radiation activity of a chloroform layer was measured. As a control, xanthosine was added to the reaction solution instead of paraxanthine or paraxanthine was removed. As a result of measurement of activity, it was found that 1.56 pmol of caffeine was produced only when paraxanthine was added as a substrate.

The above enzymatic reaction was repeated except that 7-methyl xanthine or theobromine was added to the reaction solution instead of paraxanthine. As a result of measurement of enzyme activity, production of theobromine was observed in the reaction solution to which 7-methyl xanthine was added instead of paraxanthine, while production of caffeine was observed in the reaction solution to which theobromine was added instead of paraxanthine. Regarding these results, it was revealed that the enzyme isolated in the above procedure had three different N-methyl transferase activities using two other substrates in addition to paraxanthine, respectively.

Example 10

Suppression of Caffeine Synthesis According to an Antisense Method

A recombinant vector carrying an antisense N-methyl transferase gene was constructed by the following procedure:

DNA fragments were amplified by PCR using the total length of the isolated N-methyl transferase gene as used in Example 9 as the template and the primer having the nucleotide sequences of ID SEQ NOs: 20 and 21, respectively. The ends of the DNA fragments thus amplified were changed into the blunt ends by BKL kit (TAKARA) to obtained the blunt-ended PCR-amplified fragments.

Separately, pBI vector (Clontech), to which a hygromycin resistance gene was connected, was cut with XbaI and SacI to remove the β-glucuronidase gene and the ends of the linear vector thus obtained were changed into the blunt ends.

The blunt-ended linear vector was ligated with the blunt-ended PCR amplified fragments to obtain recombinant vectors by Ligation Kit (TAKARA), and then the vector carrying the desired N-methyl transferase gene which was inserted in the reverse direction at the operable location on the downstream side of the CaMV35S promoter in the pBI vector was selected from the reaction products by sequencing. Thus, the desired recombinant vector, into which the antisense N-methyl transferase gene was inserted, was obtained and used the following transformation.

Regarding the conventional methods of biological synthesis of caffeine using coffee tissue culture, there have been many reports such as Planta, 108, 339 (1972), Plant Cell Reports, 2, 109 (1983). Coffee callus was induced from a coffee shoot apex or a young leaf according to the conventional methods. The recombinant vector was introduced into the callus thus obtained by the particle gun method. Alternatively, protoplasts of the callus were prepared by the conventional methods and the recombinant vector was introduced into the protoplasts by electroporation. After the introduction, cells having the make resistance were selected. The cells thus selected were cultured under light condition and the enzyme activity of the transformed cells was measured according to the method as described in Example 9. As a result, it was revealed that the caffeine production by the transformed cells into which the antisense N-methyl transferase gene was introduced was significantly reduced in comparison with that of the normal cells into which the antisense N-methyl transferase gene was not introduced.

Redifferentiation of the transformed coffee cells was conducted to obtain a young coffee plant, whereby the redifferentiation was carried out by conventional methods described in the reports, including Z. Pflanzenphysiol. Bd., 81, 395 (1977); and Plant Cell, Tissue and Organ Culture, 8, 243 (1987). The activity of each of the enzymes from the leaves of the young coffee plant was measured. As a result, it was revealed that caffeine production of the young coffee plant, into which the antisense N-methyl transferase was introduced, was significantly reduced in comparison with that of the young coffee plant, into which the antisense N-methyl transferase gene was not introduced.

The sequences defined by SEQ ID Numbers are as follows:

```
Phe Met Asn Arg Gly Glu Gly Glu Ser Ser Tyr Ala Gln Asn Ser    SEQ ID NO: 1
Ser Phe Thr Gln Gln Val Ala Ser Met Ala Gln Pro Ala Leu Glu
Asn Ala Val Glu Thr Leu Phe Ser Arg Asp Phe His Leu Gln Ala
Leu Asn Ala Ala Asp Leu Gly Cys Ala Ala Gly Pro Asn Thr Phe
Ala Val Ile Ser Thr Ile Lys Arg Met Met Glu Lys Lys Cys Arg
Glu Leu Asn Cys Gln Thr Leu Glu Leu Gln Val Tyr Leu Asn Asp
Leu Phe Gly Asn Asp Phe Asn Thr Leu Phe Lys Gly Leu Ser Ser
Glu Val Ile Gly Asn Lys Cys Glu Glu Val Pro Cys Tyr Val Met
Gly Val Pro Gly Ser Phe His Gly Arg Leu Phe Pro Arg Asn Ser
Leu His Leu Val His Ser Ser Tyr Ser Val His Trp Leu Thr Gln
Ala Pro Lys Gly Leu Thr Ser Arg Glu Gly Leu Ala Leu Asn Lys
Gly Lys Ile Tyr Ile Ser Lys Thr Ser Pro Val Val Arg Glu
Ala Tyr Leu Ser Gln Phe His Glu Asp Phe Thr Met Phe Leu Asn
Ala Arg Ser Gln Glu Val Val Pro Asn Gly Cys Met Val Leu Ile
Leu Arg Gly Arg Gln Cys Ser Asp Pro Ser Asp Met Gln Ser
Cys Phe Thr Trp Glu Leu Leu Ala Met Ala Ile Ala Glu Leu Val
Ser Gln Gly Leu Ile Asp Glu Asp Lys Leu Asp Thr Phe Asn Ile
Pro Ser Tyr Phe Ala Ser Leu Glu Glu Val Lys Asp Ile Val Glu
Arg Asp Gly Ser Phe Thr Ile Asp His Ile Glu Gly Phe Asp Leu
Asp Ser Val Glu Met Gln Glu Asn Asp Lys Trp Val Arg Gly Glu
Lys Phe Thr Lys Val Val Arg Ala Phe Thr Glu Pro Ile Ile Ser
Asn Gln Phe Gly Pro Glu Ile Met Asp Lys Leu Tyr Asp Lys Phe
Thr His Ile Val Val Ser Asp Leu Glu Ala Lys Leu Pro Lys Thr
Thr Ser Ile Ile Leu Val Leu Ser Lys Ile Asp Gly tgatatcact gctgtggcag ctggcctctt tgctataaaa attacttttc    SEQ ID NO: 2
tgacgaggca tggagctagc tactgcgggg aaggtgaacg aagtgttgtt
catgaacagg ggggaaggag aaagtagtta tgcacaaaac tcttctttca
cgcaacaagt ggcctcaatg gcacagccag cgctagaaaa tgcagttgaa
actctcttct ccagagattt ccaccttcaa gctcttaacg cagcggactt
gggttgtgca gcgggtccaa acacattcgc agtgatttct acgatcaaga
gaatgatgga aagaaatgc agggaattga attgccaaac actggaactt
caggtttact tgaatgatct ttttggaaat gatttcaata ccctcttcaa
aggcctgtcg tctgaggtta ttggtaacaa atgtgaggaa gttccgtgtt
atgtgatggg agtaccgggg tctttccatg gccggctttt tcctcgtaac
agcttacatt tagttcattc ctcttacagt gttcattggc ttactcaggc
accaaaagga ctcacaagca gagaaggctt ggaattaaac aaggggaaga
tttacatatc aaagacaagc cctcctgttg taagagaagc ctacttatct
```

-continued

```
caatttcatg aagatttcac aatgtttctc aatgctagat cccaagaggt
ggttccaaat ggttgtatgg tgttgatact tcgtggtagg caatgttctg
atccttcaga catgcagagc tgctttactt gggaactatt agctatggcc
attgctgaat tggtttcaca gggattgata gatgaagata aattagacac
cttcaatata cccagctatt ttgcatcact tgaggaagtg aaagatatag
tggagaggga cggatcattc acaattgatc atatagaggg gtttgatctt
gatagcgtag aaatgcagga gaatgataaa tgggttagag gggaaaagtt
taccaaggtt gtcagggcct tcacagagcc tataatttca aaccagtttg
gacctgaaat catggacaaa ctatatgaca aattcactca cattgtagtt
tcagatttgg aagcaaagct accgaagacc acaagtatca tcctagtgct
ttccaagatt gatggatagt tttttagtgt tgtgaaataa actgttgtcc
ctatcacata tatgccacta gagggttgtg ccaatgtatt gcacaagaag
atttgagagg ggtcaaatat agaaagcatt ttgctcttgt gtggagagag
aatgttttct tgatttaaat ctgtgatacc caaatcgtaa tgttgggaag
aaatgagaag ttgaacatga aattttaaaa aaaaaaaaa aaaaaaaa
aaaaaaaatt cctgcggccg cgaattc
```

```
ugauaucacu gcuguggcag cuggccucuu ugcuauaaaa auuacuuuuc     SEQ ID NO: 3
ugacgaggca uggagcuagc uacugcgggg aaggugaacg aaguguuguu
caugaacagg ggggaaggag aaaguaguua ugcacaaaac ucuucuuuca
cgcaacaagu ggccucaaug gcacagccag cgcuagaaaa ugcaguugaa
acucucuucu ccagagauuu ccaccuucaa gcucuuaacg cagcggacuu
gguugugca gcggguccaa acacauucgc agugauuucu acgaucaaga
gaaugaugga aagaaaugc agggaauuga auugccaaac acuggaacuu
cagguuuacu ugaaugaucu uuuuggaaau gauuucaaua cccucuucaa
aggccugucg ucugagguua uugguaacaa auguagaggaa guuccguguu
auguggauggg aguaccgggg ucuuuccaug gccggcuuuu uccucuguaac
agcuuacauu uaguucauuc ucuuuacagu guucauuggc uuacucaggc
accaaaagga cucacaagca gagaaggcuu ggcauuaaac aaggggaaga
uuuacauauc aaagacaagc ccuccuguug uaagagaagc cuacuuaucu
caauuucaug aagauuucac aauguuucuc aaugcuagau cccaagaggu
gguuccaaau gguuguaugg uguugauacu ucgugguagg caauguucug
auccuucaga caugcagagc ugcuuuacuu gggaacuauu agcuauggcc
auugcugaau ugguuucaca gggauugaua gaugaagaua aauuagacac
cuucaauaua cccagcuauu uugcaucacu ugaggaagug aaagauauag
uggagaggga cggaucauuc acaauugauc auauagaggg guuugaucuu
gauagcguag aaaugcagga gaaugauaaa uggguuagag gggaaaaguu
uaccaagguu gucagggccu ucacagagcc uauaauuuca aaccaguuug
gaccugaaau caugggacaaa cuauaugaca aauucacuca cauuguaguu
ucagauuugg aagcaaagcu accgaagacc acaaguauca uccuagugcu
uuccaagauu gauggauagu uuuuuagugu ugugaaauaa acuguugucc
```

-continued

```
cuaucacaua uaugccacua gaggguugug ccaauguauu gcacaagaag auuugagagg ggucaaauau agaaagcauu uugcucuugu guggagagag aauguuuucu ugauuuaaau cugugauacc caaaucguaa uguugggaag aaaugagaag uugaacauga aauuuuaaaa aaaaaaaaaa aaaaaaaaaa aaaaaaaauu ccugcggccg cgaauuc
```

Phe Met Asn Arg Gly Glu Xaa Glu Ser Ser Tyr Ala Gln Asn Ser    SEQ ID NO: 4

Gln Phe Thr Gln Val

| | |
|---|---|
| ttYatgaaYM gIggIgaRg | SEQ ID NO: 5 |
| caaaagggtc agtgctgca | SEQ ID NO: 6 |
| atgaccatga ttacgcc | SEQ ID NO: 7 |
| gccggtacct ttctggggcc | SEQ ID NO: 8 |
| ccgctgcgtt aagagcttga ag | SEQ ID NO: 9 |
| gccaaacact ggaacttcag g | SEQ ID NO: 10 |
| ccattgaggc cacttgttgc gtg | SEQ ID NO: 11 |
| ggcctgtcgt ctgaggttat tg | SEQ ID NO: 12 |
| cagcaatggc catagctaat ag | SEQ ID NO: 13 |
| ccgctgcgtt aagagcttga ag | SEQ ID NO: 14 |
| gccaaacact ggaacttcag g | SEQ ID NO: 15 |
| ccattgaggc cacttgttgc gtg | SEQ ID NO: 16 |
| ggcctgtcgt ctgaggttat tg | SEQ ID NO: 17 |
| gccatggttt acgcgca | SEQ ID NO: 18 |
| cggccatgga agaccccgg | SEQ ID NO: 19 |
| tgatatcact gctgtggcag c | SEQ ID NO: 20 |
| aaaatttaat gttcaacttc t | SEQ ID NO: 21 |
| ccattgaggc cacttgttgc gtg | SEQ ID NO: 16 |
| ggcctgtcgt ctgaggttat tg | SEQ ID NO: 17 |
| gccatggttt acgcgca | SEQ ID NO: 18 |
| cggccatgga agaccccgg | SEQ ID NO: 19 |
| tgatatcact gctgtggcag c | SEQ ID NO: 20 |
| aaaatttcat gttcaacttc t | SEQ ID NO: 21 |

What is claimed is:

1. An isolated DNA molecule comprising SEQ ID NO:2.
2. An expression vector comprising the DNA molecule of claim 1 operably linked to a plant promoter, wherein said vector expresses N-methyl transferase in plant cells.
3. A vector comprising the DNA molecule of claim 1.
4. An expression vector comprising the DNA molecule of claim 1 operably linked to a promoter that functions in a microorganism, wherein said vector expresses N-methyl transferase in the microorganism or plant.
5. An isolated RNA molecule comprising SEQ ID NO:3.
6. A vector encoding the RNA molecule of claim 5.
7. A plant cell, plant tissue, or whole plant, wherein said plant cell, plant tissue, or whole plant is transformed with the vector of claim 3 or 4.
8. The plant cell, plant tissue, or whole plant of claim 7, wherein said vector is introduced by infection.
9. A method for producing a plant secondary metabolite, wherein said method comprises:

culturing the transformed plant cell or plant tissue of claim 7 to form a plant, and culturing said plant to produce a plant secondary metabolite selected from the group consisting of 7-methyl xanthine, paraxanthine, theobromine, and caffeine, wherein said plant cell or plant tissue is a *Camellia* or a *Coffea* plant cell or plant tissue.

10. A method for modifying the concentration of caffeine in a cell, wherein said method comprises:

culturing said plant cell or plant tissue of claim 7 to form a plant, and culturing said plant to modify the concentration of caffeine, wherein said plant cell or plant tissue is a *Camellia* or a *Coffea* plant cell or plant tissue.

11. A method for producing a plant secondary metabolite, wherein said method comprises culturing the transformed whole plant of claim 7 to produce a plant secondary metabolite selected from the group consisting of 7-methyl xanthine, paraxanthine, theobromine, and caffeine, wherein said plant is a *Camellia* or a *Coffea* plant.

* * * * *